United States Patent [19]

Distler et al.

[11] 4,230,949
[45] Oct. 28, 1980

[54] TOMOGRAPHIC APPARATUS FOR PRODUCING TRANSVERSE LAYER IMAGES OF A RADIOGRAPHY SUBJECT

[75] Inventors: Walter Distler, Erlangen; Karl-Georg Heinzelmann, Neunkirchen a. Brand, both of Fed. Rep. of Germany

[73] Assignee: Siemens Aktiengesellschaft, Berlin & Munich, Fed. Rep. of Germany

[21] Appl. No.: 44,057

[22] Filed: May 31, 1979

[30] Foreign Application Priority Data

Jul. 3, 1978 [DE] Fed. Rep. of Germany ....... 2829179

[51] Int. Cl.² ............................................. A61B 6/00
[52] U.S. Cl. ................................................. 250/445 T
[58] Field of Search .................................... 250/445 T

[56] References Cited

U.S. PATENT DOCUMENTS

| | | | |
|---|---|---|---|
| 3,922,552 | 11/1975 | Ledley | 250/445 T |
| 3,986,031 | 10/1976 | Chekroun | 250/445 T |
| 4,114,040 | 9/1978 | Hounsfield | 250/445 T |
| 4,150,294 | 4/1979 | Hounsfield | 250/445 T |

Primary Examiner—Alfred E. Smith
Assistant Examiner—T. N. Grigsby
Attorney, Agent, or Firm—Hill, Van Santen, Steadman, Chiara & Simpson

[57] ABSTRACT

A radiation measuring arrangement is present which comprises a radiation source producing a radiation beam penetrating the radiography subject, and also a radiation receiver which determines the radiation intensity behind the subject. The measuring arrangement is arranged on a support which can be displaced parallel to the plane of the layer on a rotating track. A motor for driving the rotating track is also coupled with a gear ring, rotatably mounted on the rotating track so that this ring is continually rotated, while the rotating track is driven from the motor via a step by step drive unit. A gear wheel (14) is driven by the ring and in turn drives a crank for effecting displacement of the support for the measuring arrangement and also drives a further crank for a weight equalizer member. The lever arms of the cranks may be adjusted by a common motor from a remote station.

6 Claims, 3 Drawing Figures

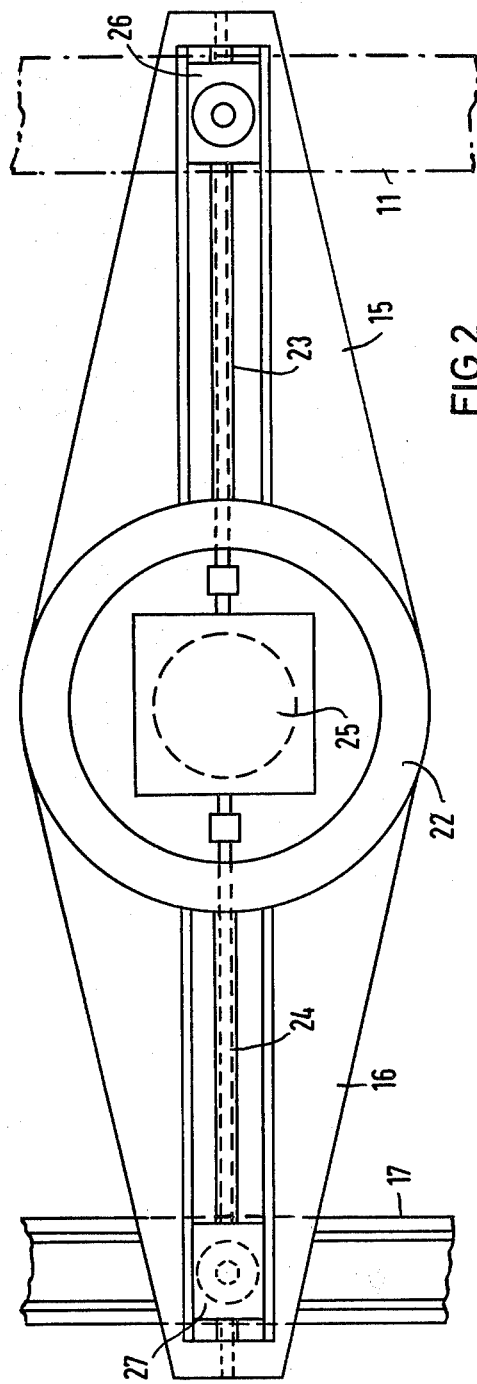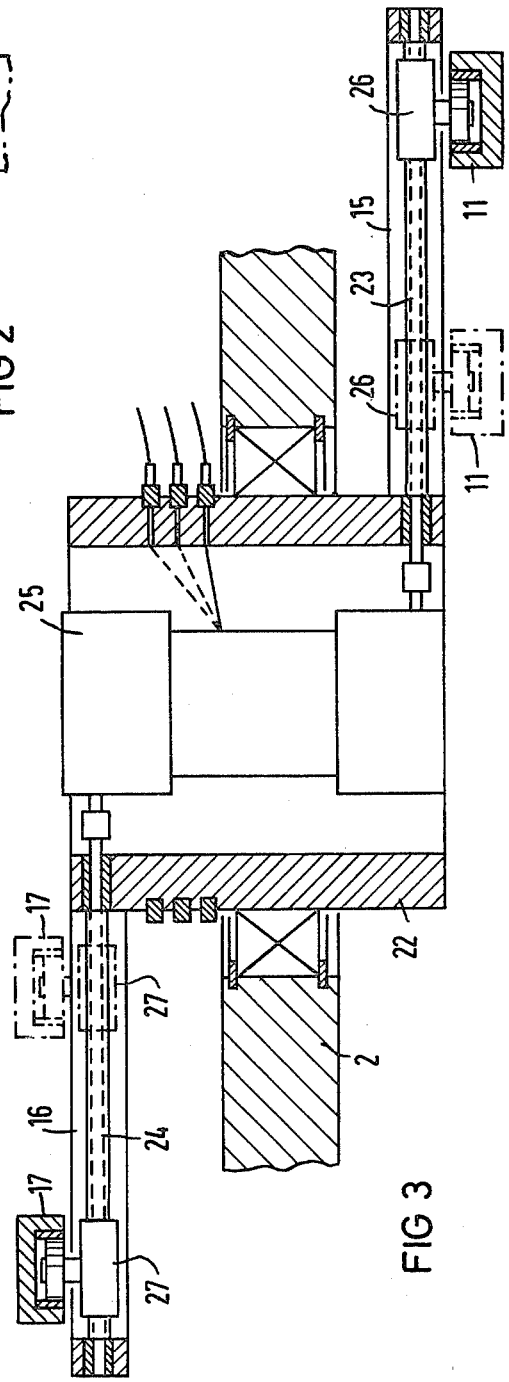

TOMOGRAPHIC APPARATUS FOR PRODUCING TRANSVERSE LAYER IMAGES OF A RADIOGRAPHY SUBJECT

BACKGROUND OF THE INVENTION

The invention relates to tomographic apparatus for producing transverse layer images of a radiography subject, having a radiation measuring arrangement which comprises a radiation source producing a radiation beam, penetrating the radiography subject, whose cross sectional extent perpendicular to the layer plane is equal to the thickness of the layer, and also a radiation receiver which determines the radiation intensity behind the subject, in which the measuring arrangement is arranged on a movable support which is displaceable in a plane parallel to the plane of the layer, and the support together with the measuring arrangement is rotatable by means of a rotating track, a motor being present for driving the rotating track for irradiating the radiography subject from different directions and for driving the support, and the apparatus having a measured value converter for transforming the signals supplied by the radiation receiver into a layer image.

A tomographic apparatus of this kind is described in the U.S. Pat. No. 3,986,031. In this apparatus belt and chain drives are provided between the drive motor and the rotating track and the support, these drives transmitting the rotary movement of the motor on the one hand to the rotating track and on the other to a crank gear with two crank wheels. The mechanical construction of this known apparatus is extremely complicated, and the apparatus is therefore expensive and prone to breakdowns.

SUMMARY OF THE INVENTION

The underlying object of the invention is to simplify the construction of a tomographic apparatus of the initially named type relative to the prior art and, more particularly, to enable the support with the measuring arrangement to remain stationary for a short while in its respective end positions so that calibration measurements may be taken in these end positions.

This object is solved according to the invention by coupling the motor with a gear ring, mounted on the rotating track, so that this gear ring may rotate continuously, while coupling the motor with the rotating track via a step by step drive unit. The gear ring drives a gear wheel and associated crank and the crank in turn drives the support. The gear wheel and crank are rotatably mounted on the rotating track and the gear wheel is in driven engagement with the gear ring. In the case of the apparatus according to the invention no belt or chain drives are necessary between the motor and the displaceable components. A suitable choice of transmission ratios renders it possible for rotary drive wheel for the crank not to be rotated about its own axis during each advance of the rotating track, so that the measuring arrangement remains stationary relative to the rotating track during a rotary step thereof. Since the support occupies an end position during each rotary step, a calibration measurement can be carried out in this end position.

An advantageous further development of the invention consists in mounting on the rotating track a weight equalizer (equilibration) member which is movable oppositely to the support with the measuring arrangement. When the support with the measuring arrangement is not moved horizontally, it is not necessary in this further development for the weight of the support with the measuring arrangement to be overcome by the crank gear because it is compensated by the weight of the equalizer member. A further development of the invention consists in the provision on the rotating track of a servomotor for adjusting the lever arms of the crank drive for the support with the measuring arrangement and the weight equalizer member. It is possible with this further development to adapt the displacement path of the support with the measuring arrangement and, if necessary, of the weight equalizer member to the dimensions of the respective radiography subject, e.g. to select a smaller displacement path for a cranial examination than for an examination of the trunk of the body.

Further details of the invention will be evident from the subclaims.

The invention is described in the following in more detail with reference to an exemplary embodiment represented in the accompanying sheets of drawings; and other objects, features and advantages will be apparent from this detailed disclosure and from the appended claims.

BRIEF DESCRIPTION OF THE DRAWINGS

FIGS. 2 and 3 show a detail of the tomograph according to FIG. 1 in a lateral view and in section.

DETAILED DESCRIPTION

Figure 1:
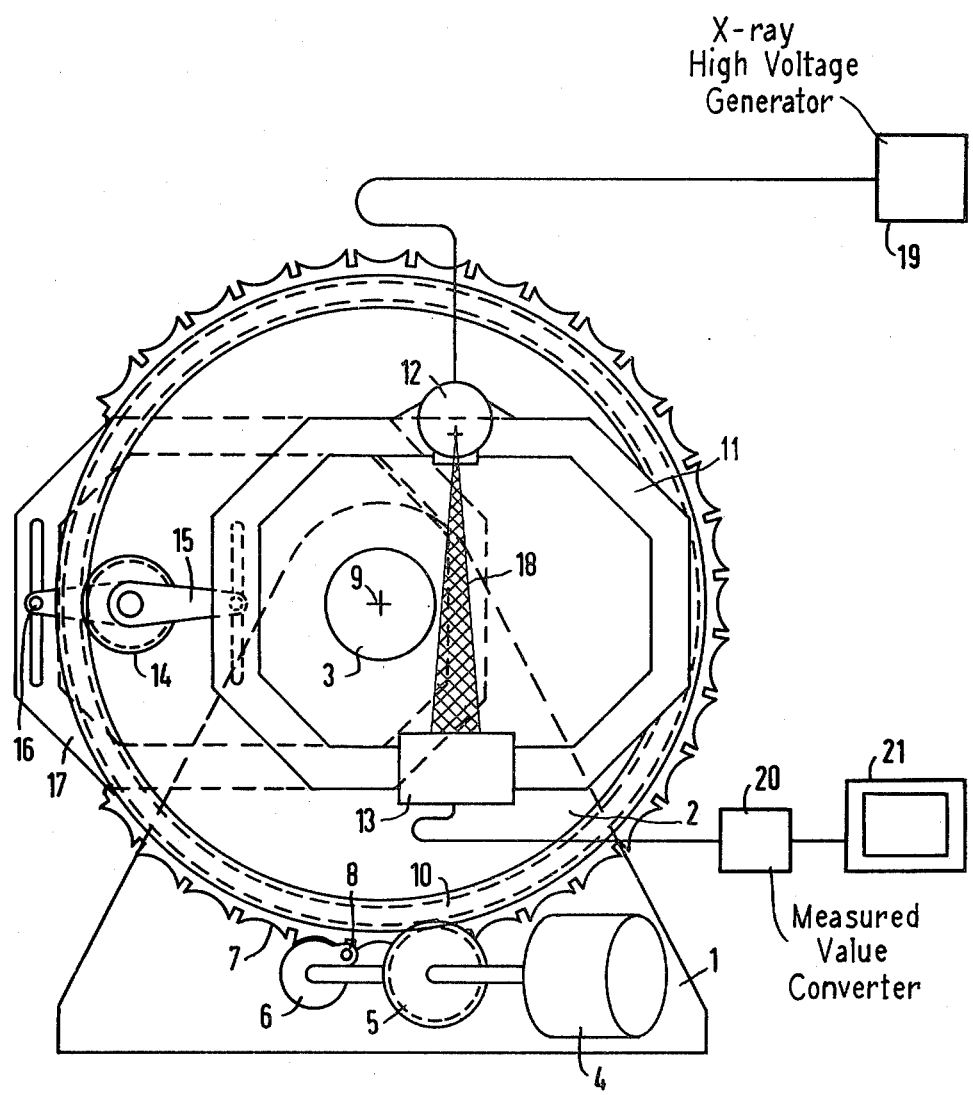
FIG. 1 shows a tomographic apparatus according to the invention.

The apparatus shown in FIG. 1 for producing transverse layer images of a radiography subject has a rotating track 2, rotatably mounted on a base 1. The base has an opening 3 into which a couch with the radiography subject can be inserted. A drive motor 4 which drives a gear wheel 5 and a Geneva drive wheel 6 is fixedly mounted on the base 1. The Geneva drive wheel 6 engages step by step in an external Geneva gearing 7 of the rotating track 2 by means of a pin 8 and thus rotates the rotating track 2 step by step about the central axis 9. The gear wheel 5 is engaged with a gear ring 10 which is mounted on the rotating track 2 so as to be freely rotatable.

A support 11 which carries an x-ray tube 12 and a radiation receiver 13 is mounted on the rotating track 2 so that it may be displaced transversely. The support 11 is periodically moved back and forth by a crank 15 attached on a gear wheel 14. The gear wheel 14 is engaged with internal gear teeth of the ring 10, while the gear wheel 5 drivingly engages with the external gear teeth of ring 10. A second crank 16 which moves a weight equalizer member 17 in an opposite sense to the support 11 with the measuring arrangement 12, 13 is attached on the gear wheel 14. What is achieved thereby is that, when the support 11 is in inclined positions, its weight does not have to be overcome by the gear wheel 14 but is balanced by the weight of member 17.

To examine a radiography subject in the opening 3, the radiation measuring arrangement 12, 13 whose x-ray tube 12 produces a radiation beam 18 which penetrates the radiography subject and whose cross sectional extent perpendicular to the layer plane is equal to the thickness of the examined layer, is displaced over the entire radiography subject by the support 11 on the rotating track 2 to scan the body layer under examination. A rotary step then takes place via the Geneva drive wheel 6 and the Geneva gearing 7. The next displacement step of the measuring arrangement 12, 13 is then effected. A succession of alternate rotary and reciprocal displacement steps of the measuring arrangement 12, 13 then takes place so that the radiography subject is penetrated from different directions. The x-ray tube 12 is supplied by an x-radiation high voltage generator 19. The signals supplied by the radiation receiver 13 during the scanning of the radiography subject, which correspond to the attenuation in the radiography subject are supplied to a measured value converter 20 which calculates an image of the examined layer of the radiography subject in such a manner that it determines the attenuation coefficients for x-radiation of specific points in the examined layer. The image thus calculated is reproduced on a visual display unit 21.

The transmission ratio of the drive units represented in FIG. 1 between the motor 4 and the Geneva gearing 7 of the rotating track 2 and also between the gear wheel 5, the ring 10 and the gear wheel 14 is selected so that the gear wheel 14 is not rotated about its own axis during a rotational step because the tangential components of movement due to the rotation of the rotating track 2 and of the ring 10 are equally great. As a result of this the support 11 with the measuring arrangement 12, 13 is stationary in its end positions during a rotational step.

As the x-radiation does not penetrate the radiation subject in these final positions, i.e. is at the side next to the opening 3, as represented in FIG. 1, calibration measurements may be carried out.

FIGS. 2 and 3 represent in detail the construction of the drive cranks 15, 16. For the sake of clarity, the gear wheel 14 which drives the crank assembly is not shown in this connection. The crank assembly 15, 16 consists of two arms which are fixedly connected with a hollow shaft 22 which is rotatably mounted in the rotating track 2 (FIG. 3) and fixedly connected with the gear wheel 14. Threaded spindles 23, 24, which can be driven by a motor 25 in the hollow shaft 22, are rotatably mounted in the respective arms of the crank assembly 15, 16. Cooperating elements 26, 27 which engage supports 11, 17 are displaceably driven by rotation of the threaded spindles 23, 24. The displacement may then take place via the motor 25 from the positions of the elements 26, 27 which are shown by solid lines to the positions shown in dotted lines (FIG. 3). In this way it is possible to alter the lever arms of the cranks 15, 16 and thus the displacement path of the supports 11, 17. It is thus possible to select, by means of the motor 25, a short displacement path, e.g. for examination of a layer of a patient's skull or a large displacement path for examining a transverse layer through the patient's trunk.

FIG. 1 represents a Geneva gear transmission as a step by step drive between the motor 4 and the rotating track 2. Other step by step drive units, e.g. worm gears may be used within the scope of the invention. The rotating track 2 is not represented in FIG. 2 for the sake of clarity.

It will be apparent that many modifications and variations may be effected without departing from the scope of the novel concepts and teachings of the present invention.

We claim as our invention:

1. A tomographic apparatus for producing transverse layer images of a radiography subject, having a radiation measuring arrangement which comprises a radiation source producing a radiation beam which penetrates the radiography subject and whose cross sectional extent perpendicular to the layer plane is equal to the layer thickness, and also a radiation receiver which determines the radiation intensity behind the subject, a movable support carrying the measuring arrangement and displaceable parallel to the plane of the layer, a rotating track carrying the movable support, and motor means for driving the rotating track for irradiating the radiography subject from various directions and for driving the movable support, and a measured value converter for transforming the signals supplied by the radiation receiver into a layer image, characterized in that a ring (10) is rotatably mounted on a common axis with the rotating track (2) and is driven by the motor means (4) for a continuous rotation of said ring (10), and a step by step drive unit (6, 7, 8) energized by the motor means (4) and driving said rotating track, a gear wheel (14) being rotatably mounted on the rotating track (2) and being driven by said ring (10), and crank means (15) driven by said gear wheel (14) for effecting movement of said movable support.

2. A tomographic apparatus according to claim 1, characterized in that the ring (10) is provided with inner and outer gear teeth and that the gear wheel (14) coupled with the crank means (15) engages with the inner gear teeth and a gear wheel (5) continuously rotated by the motor means (4) engages with the outer gear teeth of ring (10).

3. A tomographic apparatus according to claim 1, characterized in that a weight equalizer member (17) which can be moved by the gear wheel (14) in an opposite sense to the movable support (11) with the measuring arrangement (12, 13), is mounted on the rotating track (2).

4. A tomographic apparatus according to claim 1, characterized in that a servomotor (25) for adjusting the crank means (15) for the support (11) with the measuring arrangement (12, 13), and for correspondingly adjusting the range of movement of the equalizer member (17) is present on the rotating track (2).

5. A tomographic apparatus according to claim 4, characterized in that the servomotor (25) is mounted on the gear wheel (14) for driving the crank means (15, 16), threaded spindles (23, 24) of the servomotor having cooperating elements (26, 27) engaging the support (11) and the equalizer member (17) for adjusting the range of movement of the support and the equalizer member.

6. A tomographic apparatus according to claim 1, characterized in that the transmission ratios are selected so that the support (11) and member (17) remains stationary relative to the rotating track during a rotary step of the rotating track.

* * * * *